United States Patent [19]

Jolley

[11] Patent Number: 4,704,255
[45] Date of Patent: Nov. 3, 1987

[54] ASSAY CARTRIDGE

[75] Inventor: Michael E. Jolley, Round Lake, Ill.

[73] Assignee: Pandex Laboratories, Inc., Mundelein, Ill.

[21] Appl. No.: 514,170

[22] Filed: Jul. 15, 1983

[51] Int. Cl.<sup>4</sup> .............................................. B01L 3/00
[52] U.S. Cl. .................................... 422/101; 422/102; 436/177
[58] Field of Search .................... 206/509; 210/321.1, 210/416.1, 433.2, 456, 541; 422/101, 102, 103; 436/177

[56] References Cited

U.S. PATENT DOCUMENTS

| Re. 30,562 | 3/1981 | Park .................................. 422/99 X |
| 3,283,943 | 11/1966 | Cargnelutti ........................ 206/509 |
| 3,649,464 | 3/1972 | Freeman .......................... 422/99 X |
| 3,730,352 | 5/1973 | Cohen et al. .................... 210/406 X |
| 3,888,770 | 6/1975 | Avital et al. ..................... 422/101 X |
| 3,992,631 | 11/1976 | Harte . |
| 3,999,948 | 12/1976 | Deindoefer et al. . |
| 4,020,151 | 4/1977 | Bolz et al. . |
| 4,025,310 | 5/1983 | Bolz et al. . |
| 4,038,149 | 7/1977 | Liner et al. ...................... 422/102 X |
| 4,056,724 | 11/1977 | Harte . |
| 4,090,850 | 5/1978 | Chen et al. ...................... 422/102 X |
| 4,144,452 | 3/1979 | Harte . |
| 4,163,779 | 8/1979 | Harte et al. . |
| 4,167,875 | 9/1979 | Meakin ............................ 422/101 X |
| 4,184,849 | 1/1980 | Cambiaso et al. . |
| 4,189,466 | 2/1980 | Ainis et al. . |
| 4,201,763 | 5/1980 | Monthony et al. . |
| 4,238,449 | 12/1980 | Deindoerfer . |
| 4,259,289 | 3/1981 | Curry et al. . |
| 4,271,123 | 6/1981 | Curry et al. . |
| 4,295,199 | 10/1981 | Curry et al. . |
| 4,373,642 | 2/1983 | Wolters et al. .................. 206/509 X |
| 4,427,415 | 1/1984 | Cleveland ........................ 422/101 X |

OTHER PUBLICATIONS

Cleveland et al; Mobilization of Viral Antigens on Filter Paper for a Staphylococcal Protein Ammunoassay; J. Immunological Meth. 20(1979) 369-386.

Millipore; Procesing Multiple Samples with the Millipore Millititer Plate, (product publication) 1982.
D. Richman, J. of *Med. Virology*, vol. 9, pp. 299-305 (1982).
Brochure: Protein Assays & DNA Hybridization by Millipore Corporation, R. Curry, et al., *Clin. Chem.*, vol. 25, No. 9, pp. 1591-1595 (1979).
P. Cleveland, et al., *J. of Immunological Methods*, vol. 54, pp. 291-296 (1982).
P. Cleveland, et al., *J. of Clin. Microbiol*, vol. 16, No. 4, pp. 676-685 (Oct. 1982).
P. Cleveland, et al., *J. of Clin. Microbiol*, vol. 15, No. 3, pp. 402-407 (Mar. 1982).
Immunofiltration Catalog 1982-83 by V & P Scientific, Inc.
Brochure: Millititer Filtration System by Millipore Corporation.
Brochure: The Sensitivity and Precision of the Microfluor System by Dynatech Laboratories, Inc.
BRL Catalog 1981-82 (p. 134) by Bethesda Research Laboratories, Inc.
Brochure: Minifold by Schleicher & Schuell, Inc.
Brochure: V & P by V & P Scientific, Inc.

*Primary Examiner*—David L. Lacey
*Assistant Examiner*—Michael S. Gzybowski
*Attorney, Agent, or Firm*—Dorsey & Whitney

[57] ABSTRACT

An assay cartridge which has a substantially rectangular base plate, a substantially rectangular top plate, and four side walls. The top plate has a plurality of aligned adjacent reaction wells located on its top side. Each well has a hole at its bottom which opens into a waste reservoir which is the space inside of the base plate, top plate and four walls. A filter membrane is positioned against the underside of the top plate covering the well holes. A port through the base plate allows reducing the pressure in the waste reservoir relative to the pressure over the wells for drawing the liquid phase of a reaction from the well through the filter and into the waste reservoir.

26 Claims, 13 Drawing Figures

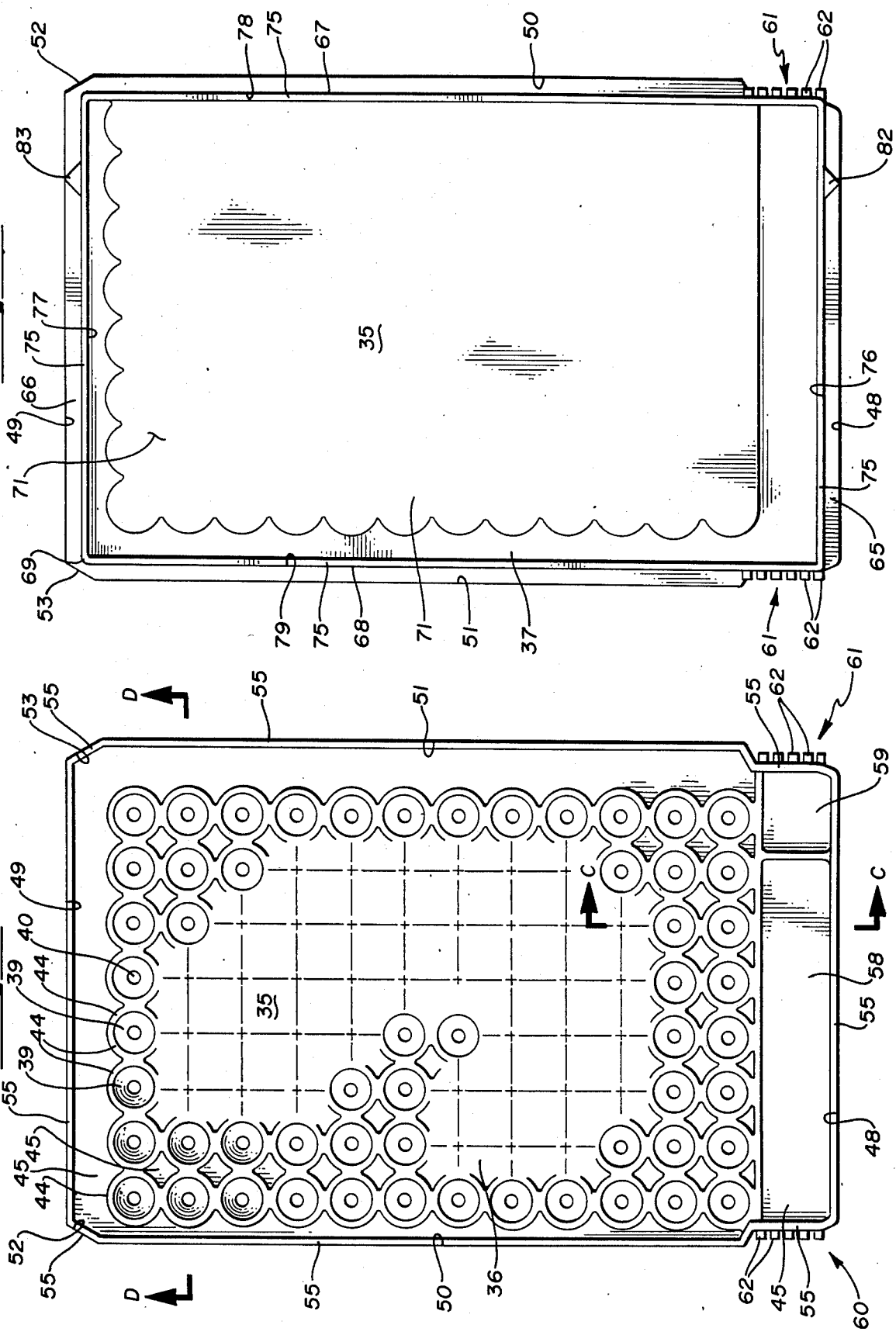

ASSAY CARTRIDGE

BACKGROUND OF THE INVENTION

This invention relates to an assay cartridge having a plurality of aligned adjacent wells which are useful as the reaction vessels for immuno-chemical reactions involving a solid phase and a liquid phase. The assay cartridge has a filter membrane located between the wells and a waste reservoir. By applying a reduced pressure to the waste reservoir, the liquid phase is drawn through the filter and into the waste reservoir. This enables convenient separation of the solid phase reaction products from liquid phase reaction products. This application is related to U.S. patent application Ser. No. 489,519 filed Apr. 28, 1983, now U.S. Pat. No. 4,652,533 which is incorporated herein by reference thereto.

A number of methods exist for the detection of substances of biological origin. One large class of methodology is the immunoassay, where antigens or haptens and their corresponding antibodies are used to probe the sample for each other. One very important variant of the immunoassay is the solid phase immunoassay. (Cf. Catt et al., *J. BIOCHEM*, 100: 31c (1966); Catt et al., *SCIENCE*, 158: 1570 (1967); U.S. Pat. No. 3,646,346 by Catt et al., these references and patents, and subsequently cited references and patents are incorporated herein by reference thereto).

Radioactive atoms, such as $^{125}I$, $^{131}I$, $^{3}H$, and $^{14}C$ for example, are commonly utilized as the label in solid phase immunoassays. The resulting solid phase radioimmunoassays are quite sensitive but suffer commonly recognized disadvantages. The radioactive nature of the label subjects the assay to stringent regulatory requirements, results in a relatively short reagent shelf life and poses a waste disposal problem.

In an attempt to overcome the disadvantages of radioimmunoassays, several alternative labeling methods have been developed. Foremost among these are the enzyme immunoassays (EIA, ELISA) where an enzyme replaces the radioactive label. (cf. U.S. Pat. No. 3,551,555 by Schuurs). Enzymes commonly utilized as labels are horseradish peroxidase, alkaline phosphatase, B-galactosidase and glucose oxidase. Enzyme immunoassays have an advantage over radioimmunoassays in that the enzyme labels are very stable and special facilities and instrumentation are not required. However, enzyme immunoassays are generally slower and more tedious to perform than radioimmunoassays.

Luminescent labels have been utilized as an alternative to radioactive or enzyme labels. (cf. U.S. Pat. No. 4,201,763 by Monthony et al.; U.S. Pat. No. 3,992,631 by Harte; U.S. Pat. No. 3,999,948 by Deindoerfer et al.; A. Coons, *FLUORESCENT ANTIBODY METHODS*; J. Danielli (Editor), *GENERAL CYTOCHEMICAL METHODS* Vol. 1). Fluorescein is the most commonly used label. Although fluorescence immunoassays possess the ease of use advantage of radioimmunoassays and the reagent stability advantage of enzyme immunoassays, prior art fluorescence immunoassays lack the sensitivity of either radioimmunoassays or enzyme immunoassays. This lack of sensitivity has significance in both research and clinical applications with the result that fluorescence immunoassays have seldom been the assay of choice in these applications.

U.S. Pat. No. 4,652,533, discloses a method of solid phase immunoassay for the quantitation of antigen, hapten or antibody analyte in a liquid sample. The solid phase immunoassay incorporates a luminescent label such as a fluorescent label, a phosphorescent label or an atomic fluorescent label. The solid phase immunoassay utilizes for example (i) a plurality of water insoluble particles of about 10 microns or less in size, or (ii) cells, to which an immunoreactant is attached. The analyte or an analyte containing reaction product is reacted with or in competition with or for the immunoreactant while the particles or cells are in a substantially suspended state. The particles or cells which have, or which through subsequent reaction will have, a luminescent label attached thereto are concentrated by microfiltration to a volume substantially less than the volume of the liquid sample which initially contained the analyte. The luminescence of substantialy all of the luminescent label attached to the concentrated particles or cells is measured.

The assay utilizes a particulate solid phase comprising cells or a plurality of water insoluble particles about 10 microns or less in size (i.e. diameter). Particles may be bacteria, mammalian cell fragments or a polymeric substrate such as, for example, polystyrene latex. Particles may be substantially transparent to a beam exciting the label and to resulting luminescence.

The speed and sensitivity of the assay are enhanced by reacting the analyte (or an analyte containing reaction product) with or in competition with or for the solid phase where the latter is suspended. The large surface area of the particulate solid phase can bring significant quantities of immunoreactants into the reaction. Substantially suspending the solid phase distributes these immunoreactants throughout the liquid medium containing the analyte (or analyte containing reaction product). This enhances rapid and complete reaction involving the analyte or analyte containing reaction product.

The solid phase of the assay may then be concentrated to a volume substantially less than the volume of the liquid sample by microfiltration. This yields a two-fold advantage. First, the analyte may be concentrated prior to quantitation, thereby increasing the sensitivity of the assays by a factor substantially identical to the concentration factor. Second, the volume of the solid phase may be concentrated to a volume where a luminescense detector such as, for example, a front face fluorometer may observe substantially all of the luminescent label.

The above discussed assay is useful for the quantitation of antigen, hapten or antibody analyte or analyte occurring on or attached to cells or other particulate material contained in liquid samples of body fluids such as, for example, serum, plasma, urine, saliva or non-body fluids such as, for example, cell culture media, potable water or waste water. Moreover, many biological substances of interest are present in particulate form in nature. Examples are bacterial antigens and mammalian cell surface antigens. The assay for quantitation of analyte occurring on or attached to cells or other particulate material is directly applicable to these systems. Furthermore, assays may be performed on living cells. Soluble proteins, haptens and viruses may be attached by known methods (cf. U.S. Pat. No. 4,201,763 by Monthony et al.) to microscopic latex particles, prepared by known procedures (cf. D. Blackley (Editor), *EMULSION POLYMERISATION* (Applied Science Publishers Ltd., Essex, England 1975)).

The foregoing assay illustrates an advance in fluorescence immunoassay methodology. This advanced methodology will be of greatest benefit to research and clinical diagnosis when automated apparatus are available for its practice. There is a need for an assay cartridge suitable for practicing the above methodology.

SUMMARY OF THE INVENTION

In accordance with the invention, an assay cartridge is provided which is useful for the quantitation of antigen, hepten or antibody analyte in a liquid sample by a solid phase immunoassay which incorporates a luminescent label such as a fluorescent label, a phosphorescent label or an atomic fluorescent label. The assay cartridge may be useful for practicing other solid phase immunoassays.

The assay cartridge comprises a substantially rectangular base plate, a substantially rectangular top plate, the top plate being located opposite to and substantially parallel to the base plate, and rear, front and first and second walls serially joined to one another and positioned between and joined to the base plate and top plate. The joined walls have a substantially rectangular cross-section.

The top plate has a plurality of aligned adjacent wells located on its top side with each well having a hole at its bottom which extends to the underside of the top plate. A waste reservoir is located beneath the wells of the top plate and inside the joined base plate, top plate and four walls. A filter membrane is positioned against the portion of the underside of the top plate to which well holes extend. Means are provided for reducing the pressure in the waste reservoir relative to the pressure over the wells while retaining any waste products in the waste reservoir.

A solid phase, for example, may react with a liquid phase in the well while the solid phase is substantially suspended in the liquid phase. Upon reducing the pressure in the waste reservoir relative to the pressure over the wells, the liquid phase will pass through the filter leaving behind the solid phase. If the well narrows near its bottom, the solid phase may be concentrated into a small area approximating the size of the filter showing through the hole in the bottom of the well. This concentration of the solid phase may be achieved where the upper walls of the wells have a cylindrical shape while the lower walls have the shape of an inverted frustrum.

The filter membrane may be joined to the portion of the underside of the top plate to which well holes extend. The means for reducing pressure in the reservoir relative to the pressure over the wells while retaining any waste products in the reservoir may comprise a port which in turn may comprise an opening through the base plate and into the waste reservoir. The port may further comprise a tube which extends into the waste reservoir in order to facilitate retaining any waste product present in that waste reservoir.

The base plate, top plate and four side walls may be constructed of molded plastic such as acrylic, polystyrene or polycarbonate. The filter may have a pore size of about 10 microns or less for the purpose of retaining upon filtration the more likely candidates for the solid phase such as those discussed above. The filter membrane may be constructed of cellulose acetate, nitrocellulose, polyvinylidene fluoride, polyvinyl chloride, teflon, polysufone, polyester, polycarbonate, paper or glass fiber.

The base plate may further comprise rear, front and first and second flat base plate lateral surfaces. The top plate further may further comprise rear, front and first and second flat top plate lateral surfaces. The rear, front and first and second walls may further comprise respectively rear, front and first and second flat wall lateral surfaces. The rear base plate lateral surface, the rear top plate lateral surface, and the rear wall lateral surface may be contiguous and substantially parallel. The front base plate lateral surface, the front top plate lateral surface, and the front wall lateral surface may be contiguous and substantially parallel. The first base plate lateral surface, the first top plate lateral surface, and the first wall lateral surface may be contiguous and substantially parallel. The second base plate lateral surface, the second top plate lateral surface, and the second wall lateral surface may be contiguous and substantially parallel.

The rear wall lateral surface may be laterally recessed relative to the rear base plate lateral surface and the rear top plate lateral surface. The front wall lateral surface may be laterally recessed relative to the front base plate lateral surface and the front top plate lateral surface. The first wall lateral surface may be laterally recessed relative to the first base plate lateral surface and the first top plate lateral surface. The second wall lateral surface may be laterally recessed relative to the second base plate lateral surface and the second top plate lateral surface.

The assay cartridge may further comprise rear and front centering pegs. The front and rear centering pegs may extend laterally outward respectively from the front and rear wall lateral surfaces and they may be substantially opposed to one another.

The base plate may further comprise first and second flat base plate corner surfaces, the first base plate corner surface being located between the first base plate lateral surface and the front base plate lateral surface. The second base plate corner surface may be located between the second base plate lateral surface and the front base plate lateral surface. The top plate may further comprise first and second top plate corner surfaces, the first top plate corner surface being located between the first top plate lateral surface and the front top plate lateral surface and the second top plate corner surface being located between the second top plate lateral surface and the front top plate lateral surface.

The top plate may further comprise a top plate raised ridge along the upper periphery of the front, rear, first and second top plate lateral surfaces and the first and second top plate corner surfaces. The base plate may further comprise a base plate raised ridge along the lower periphery of the front, rear, first and second base plate lateral surfaces and the first and second base plate corner surfaces. The top plate raised ridge and the base plate raised ridge may have substantially similar configurations and one raised ridge may have slightly smaller dimensions than the other raised ridge. The base plate may further comprise a base plate underside and a channel located (i) along the outer periphery of the base plate underside and (ii) between the base plate underside and the base plate ridge.

BRIEF DESCRIPTION OF THE FIGURES

FIG. 9 shows the top plate as viewed from above it.

FIG. 10 shows the top plate and filter membrane joined thereto as viewed from beneath the top plate and filter membrane.

DESCRIPTION OF THE PREFERRED EMBODIMENT

FIGS. 1, 2, 3 and 4 show the assay cartridge in its completely assembled form. FIGS. 5, 6, 7 and 8 show the base plate prior to such assembly. FIGS. 9, 10, 11, 12 and 13 show the top plate and the rear, front and first and second walls prior to assembly.

Figure 5:
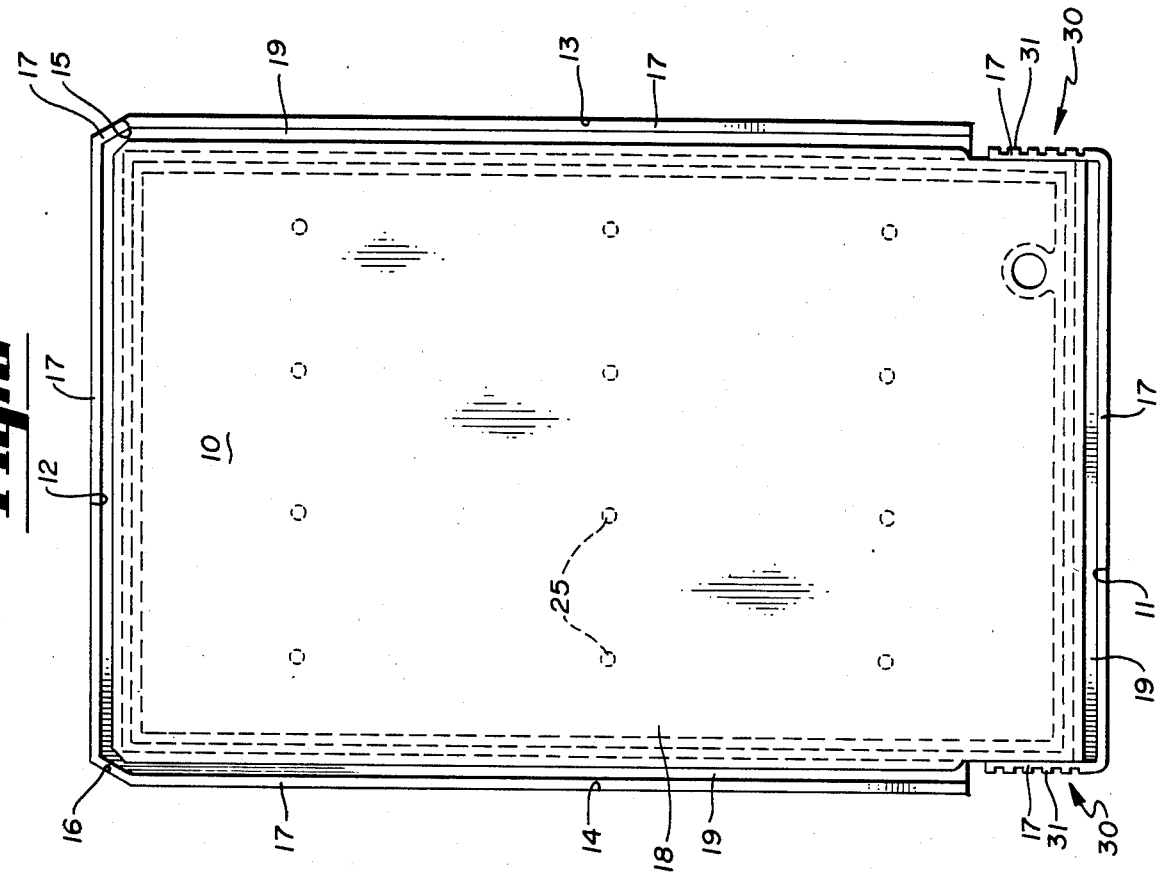
FIG. 5 shows the base plate as viewed from above it.
Figure 6:
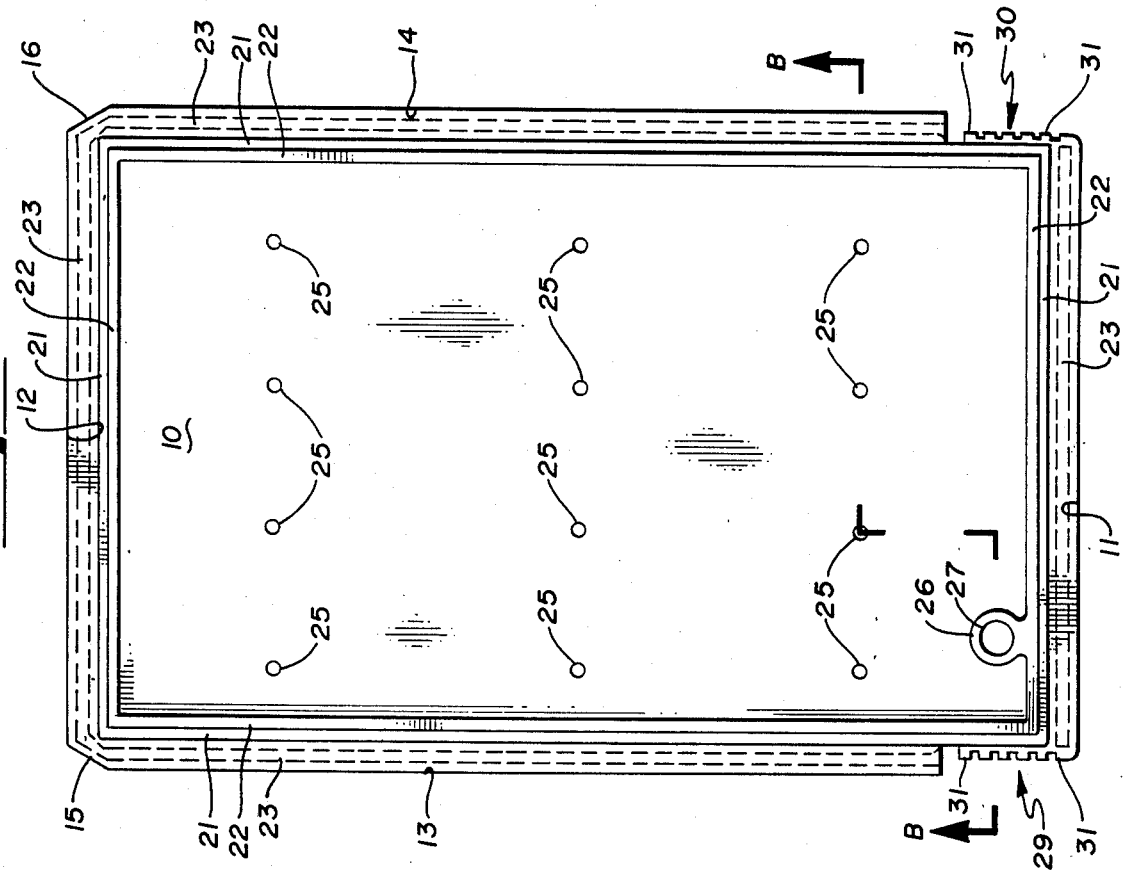
FIG. 6 shows the base plate as viewed from beneath it.

Base plate 10 has a substantially rectangular shape when viewed from the perspective of FIGS. 5 and 6. With general reference to FIGS. 2, 5, 6, 7 and 8, base plate 10 has rear 11, front 12 and first 13 and second 14 lateral surfaces. The surfaces are substantially flat. Base plate 10 has first corner surface 15 and second corner surface 16. These corner surfaces are substantially flat. First corner surface 15 is located between first lateral surface 13 and front lateral surface 12. Second corner surface 16 is located between second lateral surface 14 and front lateral surface 12.

Figure 7:
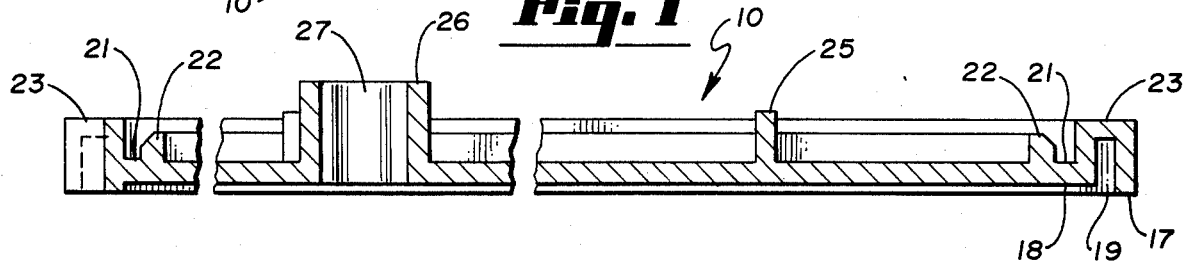
FIG. 7 is a cross-sectional view of the base plate as viewed along the section line B—B of FIG. 5.

Base plate 10 has raised ridge 17 as shown in FIGS. 6 and 7. Raised ridge 17 runs substantially along the lower periphery of front 12, rear 11, first 13 and second 14 lateral surfaces and first 15 and second 16 corner surfaces. Base plate 10 has underside 18 and channel 19 located along the outer periphery of the base plate underside 18 and between base plate underside 18 and base plate ridge 17.

Figure 8:
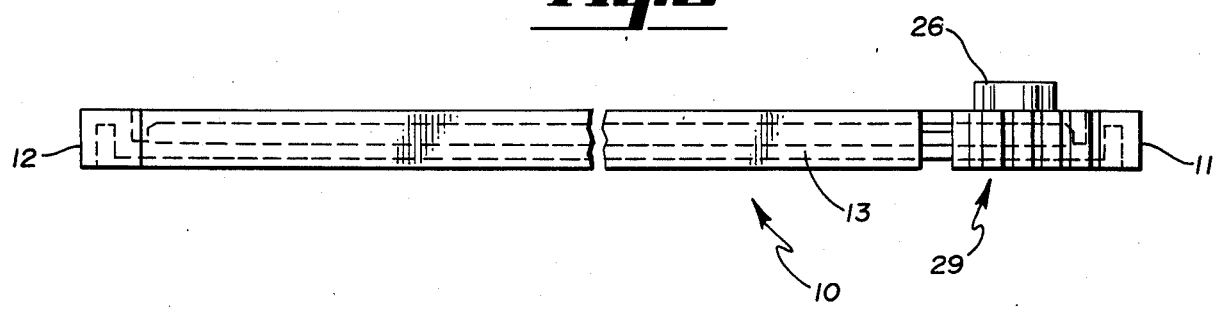
FIG. 8 shows a side view of the base plate.

Base plate 10 has seating channels 21 formed by outer ridge 23 and inner ridge 22 as shown in FIGS. 5 and 7. Base plate 10 further has a plurality of support posts 25 also as shown in FIGS. 5 and 7. Base plate 10 still further has port 26 having opening 27 through base plate 10. Port 26 in the preferred embodiment is a tube which extends above base plate 10 as shown in FIGS. 7 and 8.

Base plate 10 has finger grips 29 and 30 which are made up of a plurality of raised finger grip ridges 31.

Figure 11:
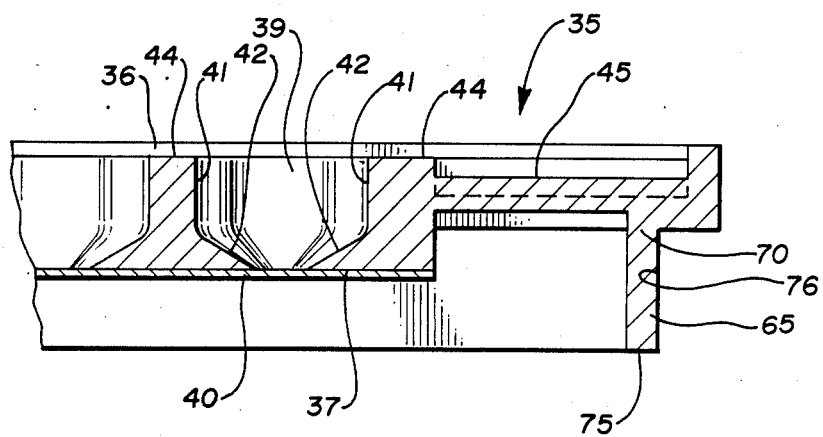
FIG. 11 shows a cross-sectional view of the top plate as viewed along the section line C—C of FIG. 9.
Figure 12:
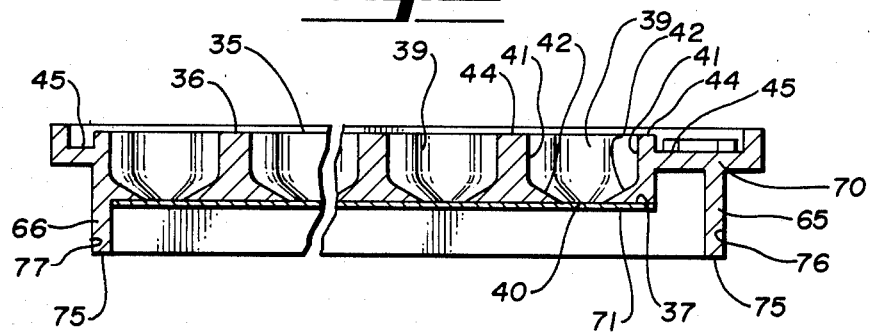
FIG. 12 shows a cross-sectional view of the top plate and filter membrane as viewed along the section line D—D of FIG. 9.
Figure 13:
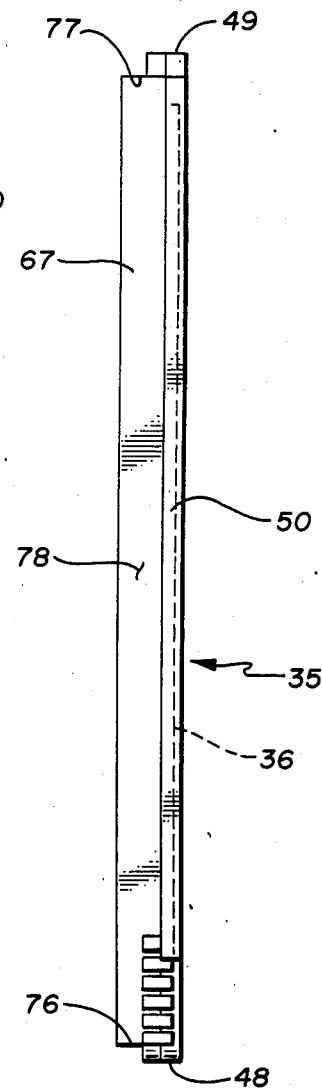
FIG. 13 shows a side view of the top plate.

Top plate 35 is shown in FIGS. 9, 10, 11, 12 and 13. Top plate 35 has a substantially rectangular shape as shown in FIGS. 9 and 10. Top plate 35 has top side 36 and underside 37. Top plate 35 has a plurality of wells 39 located on its top side 36. Wells 39 are adjacent to one another and aligned in a geometric pattern as shown in FIGS. 9, 10 and 12. In the preferred embodiment, an eight by twelve matrix of wells yields a 96 well assay cartridge. Each well 39 has a hole 40 at its bottom which extends to underside 37 of top plate 35. Wells 39 each have an upper wall 41 which has a cylindrical shape and a lower wall 42 having the shape of an inverted frustrum. Wells 39 also have a substantially circular ridge 44 which extends slightly above the base 45 of top side 36 as shown in FIGS. 9, 11 and 12. Substantially circular ridges 44 in being raised above base 45 assist in preventing reagents spilling from one well into another. Top plate 35 has rear 48, front 49 and first 50 and second 51 lateral surfaces. These lateral surfaces are substantially flat. Top plate 35 also has first 52 and second 53 corner surfaces. First corner surface 52 is located between first lateral surface 50 and front lateral surface 49. Second corner surface 53 is located between second lateral surface 51 and front lateral surface 49. Top plate 35 further has raised ridge 55 located along the upper periphery of front 49, rear 48, first 50 and second 51 lateral surfaces and first 52 and second 53 corner surfaces. Top plate 35 has two extended flat areas 58 and 59 of base 45 which are useful for placing decals on the cartridge or for placing a writing surface thereon for allowing information to be written onto the top of the plate. Top plate 35 has finger grips 60 and 61 which are constructed of a plurality of finger grip ridges 62.

With reference to FIGS. 10, 11, 12 and 13, rear 65, front 66 and first 67 and second 68 walls are shown. These walls are serially joined to one another. This is illustrated by second wall 68 being joined to front wall 66 at juncture 69. These joined walls have a substantially rectangular cross-section as shown in FIG. 10. In the preferred embodiment, walls 65, 66, 67 and 68 are shown as joined to top plate 35 prior to assembly of the cartridge. This is illustrated by rear wall 65 being joined to top plate 35 at juncture 70 as shown in FIGS. 11 and 12.

Filter membrane 71 is shown in FIGS. 10 and 12. Filter membrane 71 is positioned against the portion of underside 37 of top plate 35 to which well holes 40 extend. In the preferred embodiment, filter membrane 71 is joined to this portion of underside 37. Filter membrane 71 thus forms a seal around the periphery of each well hole 40. Filter membrane 71 is the floor of assay wells 39. In the preferred embodiment the filter membrane comprises a single filter unit. This filter unit is shown positioned against the entire portion of underside 37 to which well holes extend. In the alternative, the filter membrane may comprise a unit having holes in it where the unit holes do not align themselves with well holes 40. As a further alternative, the filter membrane may also comprise a plurality of distinct filter units where any given unit is positioned against only some of the well holes but where every well hole has some unit positioned against it.

The assay cartridge may be assembled as follows. Seating channels 21 of base plate 10 shown in FIGS. 5 and 7 receive lower end 75 of rear 65, front 66, first 67 and second 68 walls of top plate 35 as shown in FIGS. 10, 11 and 12. The assembled assay cartridge is shown in FIG. 4 where channel 21 has received the lower end of rear wall 65 and front wall 66.

Figure 4:
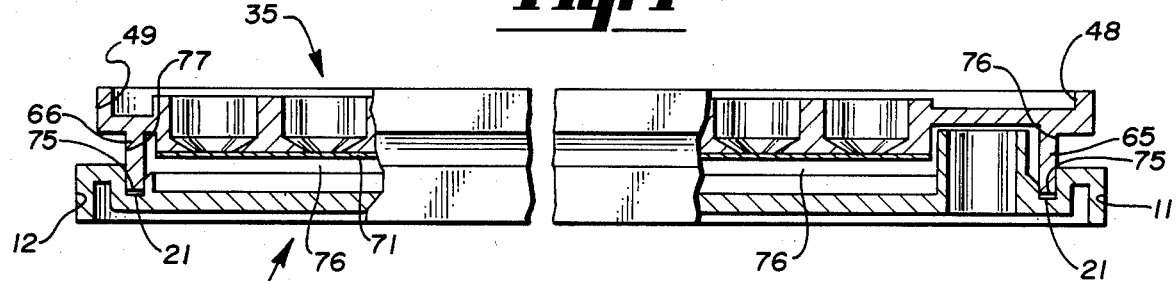
FIG. 4 shows a partial cross-sectional view of the assay cartridge as viewed along the section line A—A of FIG. 3.

In the assay cartridge's assembled state, top plate 35 is located opposite to and substantially parallel to base plate 10 as shown in FIG. 4. The serially joined rear, front, first and second walls are positioned between base plate 10 and top plate 35. These walls are joined to top plate 35 at juncture 70 as described above, and they are joined to base plate 10 at channel 21 as described immediately above. This joining of the walls to base plate 10 and top plate 35 effectively forms a sealed waste reservoir 76 which is located beneath wells 39 of top plate 35 and inside joined base plate 10, top plate 35 and the four walls. Reducing the pressure in waste reservoir 76 relative to the pressure over the wells will cause fluid in the wells to pass through filter membrane 71 and into the waste reservoir 76. Fluids passing into waste reservoir 76, i.e. waste products, will be retained in waste reservoir 76 upon a suitable choice of volume for the reservoir and an appropriate choice of the extent to which port 26 extends above base plate 10.

Rear 65, front 66, first 67 and second 68 walls have respectively rear 76, front 77, first 78 and second 79 lateral surfaces. These lateral surfaces are substantially flat as shown in FIGS. 10, 11 and 12. In the assembled assay cartridge, rear base plate lateral surface 11, rear top plate lateral surface 48 and rear wall lateral surface 76 are contiguous and substantially parallel. Front base plate lateral surface 12, front top plate lateral surface 49 and front wall lateral surface 77 are contiguous and substantially parallel. First base plate lateral surface 13, first top plate lateral surface 50 and first wall lateral surface 78 are contiguous and substantially parallel. Second base plate lateral surface 14, second top plate lateral surface 51 and second wall lateral surface 79 are contiguous and substantially parallel.

Rear wall lateral surface 76 is laterally recessed relative to rear base plate lateral surface 11 and rear top plate lateral surface 48 as shown in FIG. 4. Front wall lateral surface 77 is laterally recessed relative to front base plate lateral surface 12 and front top plate lateral surface 49 as also illustrated in FIG. 4. Similarly, but not illustrated, first wall lateral surface 78 is laterally recessed relative to first base plate lateral surface 13 and first top plate lateral surface 50. Second wall lateral surface 79 is laterally recessed relative to second base plate lateral surface 14 and second top plate lateral surface 51. This recession along the first and second walls forms a guideway for an automated device to receive the assembled assay cartridge. The recession along the front and rear walls allows an automated device to maintain proper register over the assay cartridge.

The assay cartridge may have rear 82 and front 83 centering pegs. These pegs extend laterally outward respectively from rear 76 and front 77 wall lateral surfaces. Rear 82 and front 83 centering pegs are substantially opposed to one another as shown in the preferred embodiment. These centering pegs aid an automated device in maintaining register over the assay cartridge.

Top plate raised ridge 55 and base plate raised ridge 17 have substantially similar configurations. In the preferred embodiment, top plate raised ridge 55 has slightly smaller dimensions than base plate raised ridge 17. This allows stable stacking of assay cartridges in that the top plate raised ridge of an assay cartridge will mate with the base plate raised ridge of the assay cartridge stacked on top of it. Base plate 10 also has channel 19 as a further aid in receiving and mating with a top plate raised ridge 55.

Figure 1:
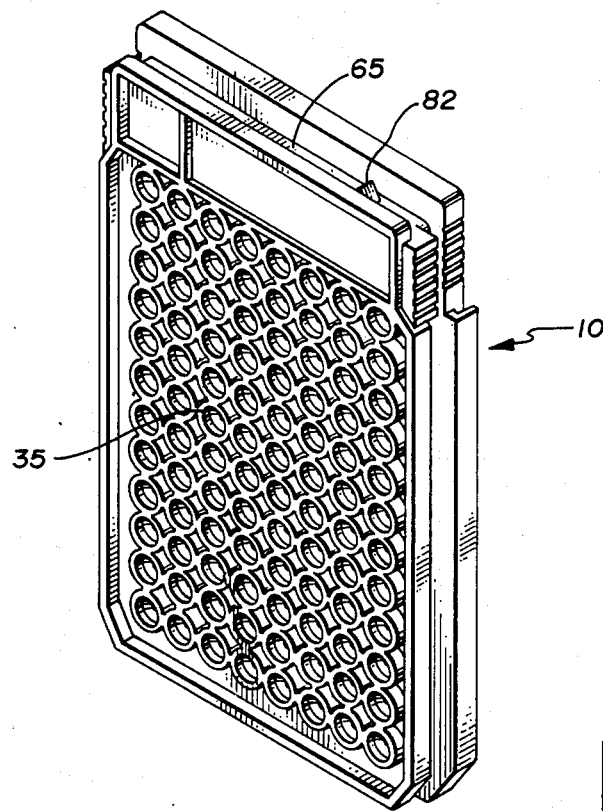
FIG. 1 shows a pictorial view of the assay cartridge, especially the top plate.
Figure 2:
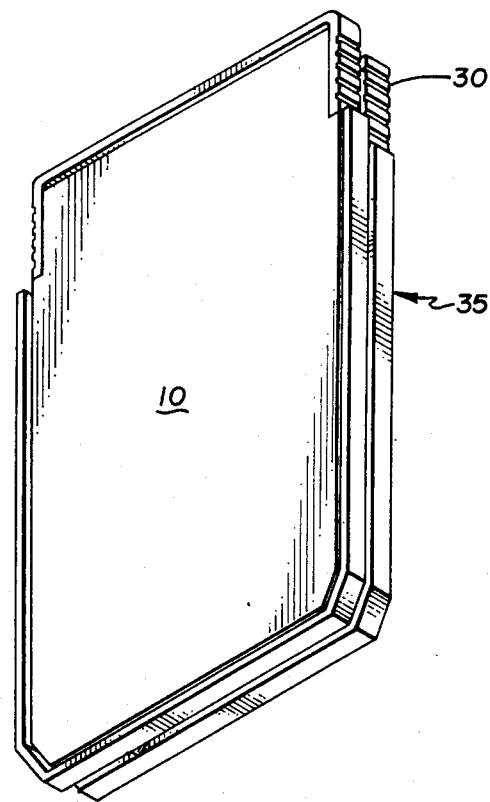
FIG. 2 shows a pictorial view of the assay cartridge, especially the base plate.
Figure 3:
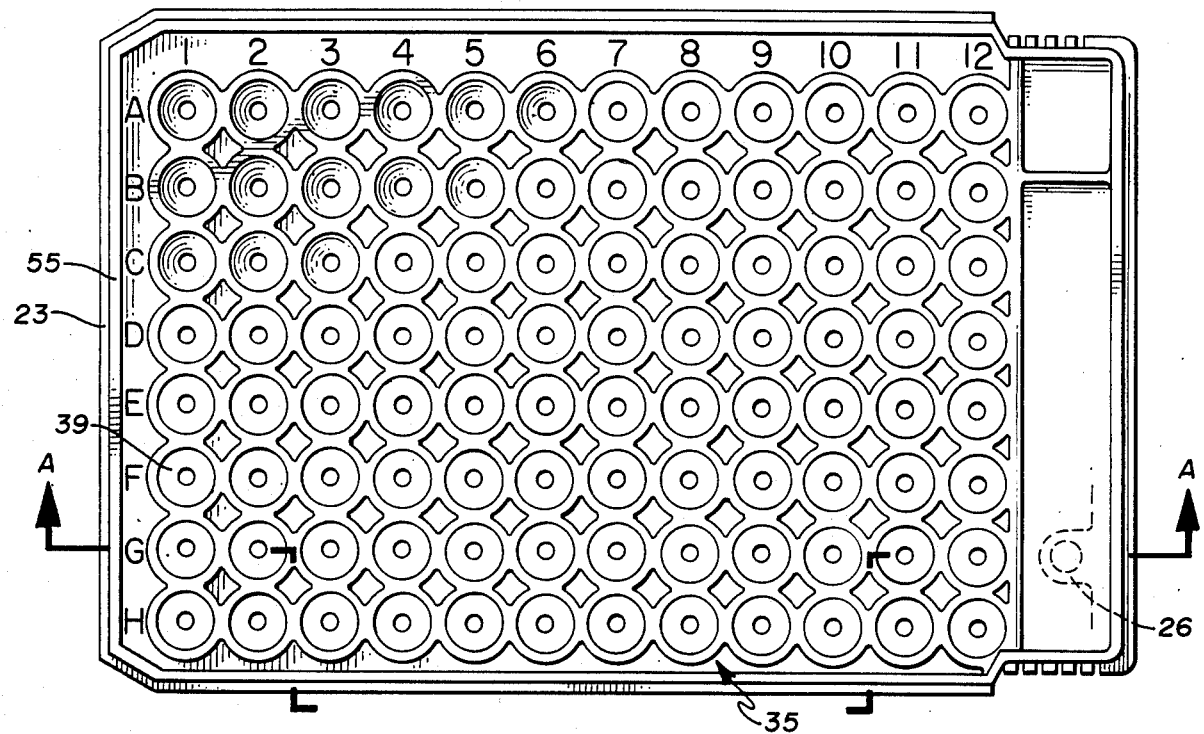
FIG. 3 shows a top view of the assay cartridge.

As shown in FIG. 3, ridge 23 of top plate 35 has a substantially similar configuration to ridge 55 of base plate 10, but ridge 23 is laterally recessed relative to ridge 55.

Base plate 10 and top plate 35 (with its joined four side walls) are injection-molded from plastic. The preferred plastic material is acrylic but other plastic materials such as, for example, polystyrene or polycarbonate could have been used as well. The filter membrane may have a pore size of about 10 microns or less depending upon the choice of solid phase. 0.2 microns is preferred in the case where the solid phase consists of beads sized above 0.2 microns. A pore size of 5–10 microns may be appropriate for a solid phase consisting of cells or other matter such as that discussed above. The filter membrane in the preferred embodiment is cellulose acetate, but nitro cellulose, polyvinyladine fluoride, polyvinyl chloride, teflon, polysulfone, polyester, polycarbonate, paper or glass fiber may, for example, also be used. These materials may be used as the filter membrane without pre-treatment. The hydrophilic/hydrophobic quality of the filter, however, may be controlled in order to prevent seepage of fluids through the filter due to head pressure alone when no reduced pressure is applied to the waste reservoir. The hydrophilic/hydrophobic quality of the filter membrane may be controlled in known ways such as, for example, treating the filter with a surfactant. As a general rule, for pore sizes of 0.2 microns for cellulose acetate, the filter may be hydrophilic. However, as pore diameters get larger such as in the 5–10 micron range, the filter may be hydrophobic.

In the preferred embodiment, the well hole has a diameter of approximately 2 mm, the upper wall of the well has a diameter of about 6.9 mm, and the well has a total depth from the top of the upper wall to the hole of about 4.25 mm. These dimensions represent a compromise between a greater depth which allows adding a greater quantity of reagents to the well and a lower depth vis-a-vis the diameter of the upper wall which would allow a broader cone of excitation and emission light to clear the top of the well in reaching and exiting from the concentrated filtered solid phase.

The filter membrane is joined to the top plate by placing the filter membrane into the mold prior to injecting and molding the plastic into the form of a top plate. The walls and base plate may be joined together ultrasonically where causing the top plate to vibrate in turn causes heat to be generated at the point of contact. Upon sufficient heat being generated at the point of contact, the lower end of the four side walls will fuse with the base plate channel receiving the lower end of the four side walls. Alternatively, a seal could be formed using solvents or another source of heat. Furthermore, the side walls could be joined to the base plate at the molding stage and the side walls subsequently joined to the top plate ultrasonically. Still further alternatives in joining the side walls to one another and to the base plate and top plate are intended to come within the spirit of the present invention.

The invention may be embodied in other specific forms than those set forth in this specification without departing from the spirit or essential characteristics thereof. Present embodiments, therefore, are to be considered in all respects as illustrative and not restrictive, the scope of the invention being indicated by the appended claims rather than by the foregoing descriptions, and all changes which come within the meaning and range of equivalency of the claims are therefore intended to be embraced therein.

I claim:

1. A fully disposable assay cartridge for conducting a pluralilty of solid phase fluorescence immunoassays on materials in which such assays are conducted within said cartridge itself and during the application of reduced pressure in a waste reservoir, said cartridge comprising:

a substantially rectangular base plate;

a substantially rectangular top plate having a top side and an underside, the top plate located opposite to and substantially parallel to the phase, the top plate having a plurality of aligned adjacent wells located on its top side, each well having a top opening with an edge intersecting said top side and a bottom hole at its bottom which extends to the underside of the top plate, said bottom hole of said well being smaller than said top opening, said wells further having lower walls having an inverted frustum shape with a tapered portion extending downwardly and inwardly toward said bottom hole and substantially terminating at, and defining, said bottom hole for concentrating material on which an assay is to be conducted at said bottom hole, and relative top opening, bottom hole and depth dimensions for conduction a solid phase fluorescence immunoassay in said wells including said bottom hole having a diameter no greater than one-half the diameter of said top opening and said depth dimension being sufficiently small relative to said top opening to permit excitation light to clear the edge of said top opening and excite the material concentrated at said bottom hole and to permit emission light from the material concentrated at said bottom hole to clear the edge of said top opening so that the same can be measured;

an intermediate section comprising rear, front and first and second walls having substantially rectangular cross sections and being serially and permanently joined to one another in sealed relationship, said intermediate section positioned between and permantly joined to said base plate and said top plate in sealed relationship to define a cavity between said base and top plates and said intermediate section;

a sealed waste reservoir located beneath the wells of the top plate and inside the cavity defined by the permanently joined base plate, top plate and intermediate section;

a non-removable filter membrane permanently affixed to the underside of the top plate to which said well holes extend, said membrane extending across said bottom hole and being permanently affixed in sealing relationship to the underside of said top plate in an area surrounding said bottom hole whereby an effective filter area for each well is defined by the size of said bottom hole; and means for facilitating a reduction of pressure in the waste reservoir relative to the pressure over the wells while retaining any waste products in the waste reservoir comprising a port in said waste reservoir, said means facilitating the simultaneous reduction of pressure in said waste reservoir and for conducting a solid phase immunoassay.

2. The assay cartridge of claim 1 wherein the port further comprises a tube which extends into the waste reservoir.

3. The assay cartridge of claim 1 wherein the filter membrane has a pore size of about 10 microns of less.

4. The assay cartridge of claim 1 wherein the base plate, top plate, and intermediate section are molded plastic.

5. The assay cartridge of claim 4 wherein the plastic is acrylic, polystryrene, or polycarbonate.

6. The assay cartridge of claim 5 wherein the filter membrane is cellulose acetate, nitrocellulose, polyvinylidene fluoride, polyvinyl chloride, teflon, polysugone, polyester, polycarbonate, paper or glass fiber.

7. The assay cartridge of claim 1 wherein
the base plate further comprises rear, front and first and second flat base plate lateral surfaces,
the top plate further comprises rear, front and first and second flat top plate lateral surfaces,
the rear, front and first and second walls further comprise respectively rear, front and first and second flat wall lateral surfaces,
the rear base plate lateral surface, the rear top plate lateral surface, and the rear wall lateral surface being contiguous and substantially parallel,
the front base plate lateral surface, the front top plate lateral surface, and the front wall lateral surface being contiguous and substantially parallel,
the first base plate lateral surface, the first top plate lateral surface, and the first wall lateral surface being contiguous and substantially parallel, and
the second base plate lateral surface, the second top plate lateral surface, and the second wall lateral surface being contiguous and substantially parallel.

8. The assay cartridge of claim 7 wherein
the rear wall lateral surface is laterally recessed relative to the rear base plate lateral surface and the rear top plate lateral surface,
the front wall lateral surface is laterally recessed relative to the front base plate lateral surface and the front top plate lateral surface,
the first wall lateral surface is laterally recessed relative to the first base plate lateral surface and the first top plate lateral surface, and
the second wall lateral surface is laterally recessed relative to the second base plate lateral surface and the second top plate lateral surface.

9. The assay cartridge of claim 8 wherein the assay cartridge further comprises rear and front centering pegs, said rear and front centering pegs extending laterally outward respectively from the rear and front wall lateral surfaces and being substantially opposed to one another.

10. The assay cartridge of claim 7 wherein
the base plate further comprises first and second flat base plate corner surfaces, the first base plate corner surface located between the first base plate lateral surface and the front base plate lateral surface, the second base plate corner surface located between the second base plate lateral surface and the front base plate lateral surface, and
the top plate further comprises first and second top plate corner surfaces, the first top plate corner surface located between the first top plate lateral surface and the front top plate lateral surface, the second top plate corner surface located between the second top plate lateral surface and the front top plate lateral surface.

11. The assay cartridge of claim 10 wherein
the top plate further comprises a top plate raised ridge along the upper periphery of the front, rear, first and second top plate lateral surfaces and the first and second top plate corner surfaces,
the base plate further comprises a base plate raised ridge along the lower periphery of the front, rear, first and second base plate lateral surfaces and the first and second base plate corner surfaces, and
the top plate raised ridge and the base plate raised ridge having substantially similar configurations and one raised ridge having slightly smaller dimensions than the other raised ridge.

12. The assay cartridge of claim 11 wherein the base plate further comprises a base plate underside and a channel located along the outer periphery of the base plate underside and between the base plate underside and the base plate ridge.

13. A fully disposable assay cartridge for conducting a plurality of solid phase fluorescenc immunoassays on materials in which such assays are conducted within said cartridge itself and during the application of reduced pressure in a waste reservoir, said cartridge comprising:
a top plate having a top side and a bottom side;
a plurality of assay wells disposed in said top plate, each of said wells extending through said top plate and having a top opening with an edge intersecting said top side, a bottom opening in said bottom side and a side wall portion having the shape of an inverted frustum and extending toward said bottom opening and substantially terminating at and defining said bottom opening, said bottom opening being smaller than said top opening and said side wall portion including a tapered portion tapering inwardly toward said bottom opening to intersect with said bottom opening for concentrating material on which an assay is to be conducted at said bottom opening, said wells having relative top opening, bottom opening and depth dimensions for conducting a plurality of said phase fluorescence immunoassays in said wells including said bottom opening having a diameter no greater than one-half the diameter of said top opening and said depth dimension being sufficiently small relative to said top opening to permit excitation light to clear the edge of said top opening and excite the material concentrated at said bottom opening and to permit emission light from the material concentrated at said bottom opening to clear the edge of said top opening so that the same can be measured;
a non-removable membrane extending across said bottom opening and being permanently affixed in sealing relationship to the bottom side of said top plate in an area surrounding the bottom opening of each of said wells whereby an effective filter area for each well is defined by the size of said bottom opening;
a base plate permanently connected with said top plate in sealed relationship so as to form a sealed waste reservoir between said base plate and the bottom side of said top plate; and
a port in said waste reservoir for facilitating a reduction of pressure in said waste reservoir relative to the pressure in said wells, said port facilitating the simultaneous reduction of pressure in said waste reservoir and for conducting a solid phase immunoasay.

14. The assay cartridge of claim 13 including a raised ridge surrounding the top opening of each of said wells.

15. The assay cartridge of claim 13 wherein the diameter of said bottom opening is less than one-third the diameter of said top opening.

16. The assay cartridge of claim 13 wherein said tapered portion extends inwardly to said bottom opening.

17. The assay cartridge of claim 13 wherein said waste reservoir is permanently sealed.

18. The assay cartridge of claim 13 wherein the side wall portion of each of said wells includes a cylindrical portion adjacent to said top opening and said tapered portion extends between said cylindrical portion and said bottom opening.

19. The assay cartridge of claim 18 wherein said tapered portion forms an acute angle with respect to longitudinal exis of said well.

20. The assay cartridge of claim 13 wherein said top opening has a diameter greater than the depth of said wells.

21. The assay cartridge of claim 20 wherein said top opening is approximately 6.9 mm in diameter, said bottom opening is approximately 2 mm in diamter and the depth of each of said wells is approximately 4.25 mm.

22. A fully disposable assay cartridge for conducting a plurality of solid phase fluorescence immunoassays on materials in which such assays are conducted within said cartridge itself and during the application of reduced pressure in a waste reservoir, said cartridge comprising:
a top plate having a top side and a bottom side;
a plurality of assay wells disposed in said top plate, each of said wells extending through said top plate and having a top opening with an edge intersecting said top side, a bottom opening in said bottom side and a side wall extending between said top and bottom openings comprising a lower tapered side wall portion having the shape of an inverted frustum and substantially terminating at and defining said bottom opening, said bottom opening being smaller than said top opening and said side wall including a tapered portion which tapers inwardly toward said bottom opening for concentrating material on which an assay is to be conducted at said bottom opening, said wells having relative top opening, bottom opening and depth dimensions for conducting a plurality of solid phase fluorescence immunoassays in said wells;
a single sheet of filter membrane permanently fixed to the bottom side of said top plate in an area surrounding the bottom opening of each of said wells so as to preclude the passage of fluid through said bottom opening except through said filter membrane, said membrane extending across said bottom openings and being permanently affixed in sealing relationship to the underside of said bottom openings in the area surrounding said bottom openings whereby an effective filter area for each well is defined by the size of said bottom opening;
a base plate permanently connected with said top plate in sealed relationship so as to form a sealed waste reservoir between said base plate and the bottom side of said top plate; and
a port in said waste reservoir for facilitating a reduction of pressure in said waste reservoir relative to the pressure in said wells, said port facilitating the simultaneous reduction of pressure in said waste reservoir and for conducting a solid phase immunoassay.

23. The assay cartridge of claim 22 wherein said filter membrane is joined to the bottom side of said top plate in an area surrounding the bottom opening of each of said wells.

24. The assay cartridge of claim 23 wherein said filter membrane is bonded to the bottom side of said top plate and maintained in such position solely by said bonding.

25. The assay cartridge of claim 23 wherein said filter membrane is joined with the underside of said top plate by molding the underside of said top plate directly to said filter membrane.

26. The assay cartridge of claim 25 wherein said filter membrane is maintained in position against the bottom side of said top plate solely as a result of said molding.

* * * * *

UNITED STATES PATENT AND TRADEMARK OFFICE
CERTIFICATE OF CORRECTION

PATENT NO. : 4,704,255
DATED : November 3, 1987
INVENTOR(S) : Michael E. Jolley

It is certified that error appears in the above-identified patent and that said Letters Patent is hereby corrected as shown below:

In column 9, line 3, delete "phase" and insert --base plate--.

In column 9, line 17, delete "conduction" and insert --conducting--.

In column 9, line 33, delete "permantly" and insert --permanently--.

In column 10, line 1, delete "polysugone" and insert --polysufone--.

In column 11, line 9, delete "fluorescenc" and insert --fluorescence--.

In column 11, line 29, delete "said" and insert --solid--.

Signed and Sealed this

Nineteenth Day of July, 1988

Attest:

DONALD J. QUIGG

*Attesting Officer*  *Commissioner of Patents and Trademarks*